US010865164B2

(12) United States Patent
Peitz et al.

(10) Patent No.: US 10,865,164 B2
(45) Date of Patent: Dec. 15, 2020

(54) PROCESS FOR OLIGOMERIZATION WITH STAGE-CUSTOMIZED EXCHANGE OF THE OLIGOMERIZATION CATALYST

(71) Applicant: Evonik Operations GmbH, Essen (DE)

(72) Inventors: Stephan Peitz, Oer-Erkenschwick (DE); Dietrich Maschmeyer, Recklinghausen (DE); Helene Reeker, Dortmund (DE); Guido Stochniol, Haltern am See (DE); Markus Winterberg, Waltrop (DE); Andreas Beckmann, Recklinghausen (DE)

(73) Assignee: Evonik Operations GmbH, Essen (DE)

(*) Notice: Subject to any disclaimer, the term of this patent is extended or adjusted under 35 U.S.C. 154(b) by 0 days.

(21) Appl. No.: 16/711,012

(22) Filed: Dec. 11, 2019

(65) Prior Publication Data

US 2020/0189993 A1 Jun. 18, 2020

(30) Foreign Application Priority Data

Dec. 13, 2018 (EP) ..................................... 18212258

(51) Int. Cl.
| | | |
|---|---|---|
| *C07C 2/10* | (2006.01) | |
| *B01J 38/02* | (2006.01) | |
| *B01J 38/48* | (2006.01) | |
| *C07C 7/04* | (2006.01) | |
| *B01J 8/02* | (2006.01) | |
| *B01J 8/04* | (2006.01) | |
| *B01J 19/18* | (2006.01) | |
| *B01J 19/24* | (2006.01) | |
| *C07C 7/00* | (2006.01) | |

(52) U.S. Cl.
CPC ................. *C07C 2/10* (2013.01); *B01J 38/02* (2013.01); *B01J 38/485* (2013.01); *C07C 7/04* (2013.01); *B01J 8/02* (2013.01); *B01J 8/04* (2013.01); *B01J 8/0419* (2013.01); *B01J 19/1818* (2013.01); *B01J 19/1825* (2013.01); *B01J 19/1837* (2013.01); *B01J 19/24* (2013.01); *B01J 19/242* (2013.01); *B01J 19/2415* (2013.01); *B01J 19/2425* (2013.01); *C07C 7/005* (2013.01); *C07C 2521/12* (2013.01); *C07C 2523/78* (2013.01)

(58) Field of Classification Search
CPC .. C07C 2/10; C07C 7/04; C07C 7/005; C07C 2521/12; C07C 2523/78; B01J 38/02; B01J 38/485; B01J 8/02; B01J 8/0419; B01J 19/1818; B01J 8/04; B01J 19/1825; B01J 19/2415; B01J 19/242; B01J 19/1837; B01J 19/24; B01J 19/2425; B01J 23/002; B01J 23/78; B01J 35/1019; B01J 35/1023; B01J 2523/00; C10G 50/00

See application file for complete search history.

(56) References Cited

U.S. PATENT DOCUMENTS

| | | | | |
|---|---|---|---|---|
| 4,547,602 A | * | 10/1985 | Tabak .................... | C10G 69/02 585/314 |
| 5,177,282 A | * | 1/1993 | Nierlich .................... | C07C 7/13 585/329 |
| 6,846,965 B1 | | 1/2005 | Schulz et al. | |
| 7,161,054 B2 | | 1/2007 | Heidemann et al. | |
| 2004/0181105 A1 | * | 9/2004 | Heidemann ............... | C07C 2/10 585/531 |
| 2016/0194257 A1 | * | 7/2016 | Lilga ....................... | B01J 23/42 585/255 |
| 2016/0194572 A1 | * | 7/2016 | Lilga ....................... | C07C 2/66 585/14 |
| 2016/0221894 A1 | * | 8/2016 | Xu ......................... | C10G 45/40 |
| 2017/0152448 A1 | * | 6/2017 | Pucci ..................... | C10G 50/00 |
| 2017/0240821 A1 | * | 8/2017 | Fei ......................... | C10L 1/08 |

FOREIGN PATENT DOCUMENTS

| | | |
|---|---|---|
| DE | 199 22 038 | 11/2000 |
| DE | 10 2009 027 408 | 1/2011 |
| EP | 0 395 857 | 11/1990 |
| EP | 1 457 475 | 9/2004 |

OTHER PUBLICATIONS

U.S. Appl. No. 16/710,784, filed Dec. 11, 2019, Stephan Peitz et al.
European Search Report dated Mar. 3, 2020 in European Application 19213910.3.

* cited by examiner

*Primary Examiner* — Ali Z Fadhel
(74) *Attorney, Agent, or Firm* — Grüneberg and Myers PLLC

(57) ABSTRACT

A method includes at least two-stage process for the oligomerization of short-chain olefins in the presence of a catalyst, wherein the regeneration of the catalyst is stage-customized.

14 Claims, No Drawings

PROCESS FOR OLIGOMERIZATION WITH STAGE-CUSTOMIZED EXCHANGE OF THE OLIGOMERIZATION CATALYST

CROSS-REFERENCE TO A RELATED APPLICATION

The present application claims the benefit to the European application EP 18212258.0, filed on Dec. 13, 2018, which is incorporated by reference in its entirety.

BACKGROUND OF THE INVENTION

Field of the Invention

The present invention relates to an at least two-stage process for the oligomerization of short-chain olefins in the presence of a catalyst, wherein the catalyst regeneration is stage-customized.

Discussion of the Background

Oligomerization is generally understood as meaning the reaction of unsaturated hydrocarbons with themselves to form correspondingly longer-chain hydrocarbons, the so-called oligomers. Thus, for example, an olefin having six carbon atoms (hexene) can be formed by oligomerization of two olefins having three carbon atoms. The oligomerization of two molecules with one another is also referred to as dimerization.

The resulting oligomers are intermediates that are used, for example, for producing aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

Processes for oligomerizing olefins are sufficiently well known in the related art and are used on an industrial scale. The production quantities amount to several thousand kilotons per year in Germany alone. In order to ensure highest possible conversions and as far as possible continuous operation of oligomerization processes, industrial plants usually comprise not just one, but at least two reaction stages connected in series. As a result, the oligomerization process can be kept in operation even in the case of failure of one reaction stage.

The catalysts used in the oligomerization of olefins have high activities and are sometimes adjusted to the particular oligomerization process. However, the catalysts used lose activity over time by aging and/or poisoning and the conversions to the desired oligomers decrease. For this reason oligomerization catalysts are typically exchanged for a fresh oligomerization catalyst at an interval of about 4 to 6 years (48 to 72 months) in all reaction stages.

In the known exchange of oligomerization catalyst, the reactor of the first reaction stage is first emptied and fresh catalyst is used. The fresh catalyst may in this case be an already used but regenerated catalyst or a newly produced catalyst. During the exchange of the catalyst in the first reaction stage, the starting mixture comprising the olefins to be oligomerized is diverted around the first reaction stage and the reactor(s) of the following reaction stage(s) continue in operation. After successful exchange of the catalyst material in the first reaction stage, this is again put into operation and immediately after, the reactor(s) of the second reaction stage are bypassed and their catalyst exchanged. Then follow, in the same way, the optionally present third and optional further reaction stages.

As a consequence of such an exchange concept, the plant is operated for a long period, namely from the beginning to the end of the exchange of the catalyst in each individual reaction stage, with one less reaction stage than in normal operation. This results in correspondingly long ongoing conversion losses. The handling of the catalyst prior to filling into the reactor can also result in prolonging the start-up time, i.e. the time required for the catalyst in order to achieve the desired conversions and also product qualities. Together with the problems mentioned with catalyst exchange, the result overall is a considerable decline in conversion and over a relatively long time period. Also for economic reasons, such a situation is undesirable.

SUMMARY OF THE INVENTION

The object of the present invention was to provide a process having at least two reaction stages for oligomerization of olefins which does not have the aforementioned problems. The basic object of the present invention was achieved with the process for oligomerization according to embodiment 1. Preferred configurations are specified in further embodiments below.

1. Process for oligomerization of $C_3$- to $C_6$-olefins, in which a starting mixture is used comprising the $C_3$- to $C_6$-olefins and from which nitrogen-, oxygen- and/or sulfur-containing impurities that act as catalyst poisons have been at least partially removed, wherein the oligomerization is carried out in at least two successive reaction stages, which each consist of at least one reactor and at least one distillation column, in each case using an oligomerization catalyst having a composition of 15 to 40% by weight NiO, 5 to 30% by weight $Al_2O_3$, 55 to 80% by weight $SiO_2$ and 0.01 to 2.5% by weight of an alkali metal oxide, and wherein at least the reactor(s) of the first reaction stage are operated isothermally, characterized in that the oligomerization catalyst in the first reaction stage is exchanged for a fresh oligomerization catalyst at the latest after 47 months, preferably at the latest after 45 months, particularly preferably at the latest after 43 months, and the oligomerization catalyst in the following reaction stage(s) is exchanged for a fresh oligomerization catalyst at the earliest after 48 months to at the latest after 72 months.

2. Process for the oligomerization according to embodiment 1, wherein the oligomerization catalyst in the first reaction stage is exchanged for a fresh oligomerization catalyst at the earliest after 6 months.

3. Process for the oligomerization according to embodiment 1 or 2, wherein the process comprises three, four or five reaction stages.

4. Process for the oligomerization according to embodiment 3, wherein the catalyst of the second and all subsequent reaction stages are exchanged at the same time.

5. Process for the oligomerization according to any of embodiments 1 to 4, wherein the reactor(s) in each reaction stage are operated isothermally.

6. Process for the oligomerization according to any of embodiments 1 to 5, wherein the volume of the reactor(s) of the second and each further reaction stage is equal to the volume of the preceding reaction stage or is in each case smaller than that of the preceding reaction stage.

7. Process for the oligomerization according to any of embodiments 1 to 6, wherein the fresh oligomerization catalyst is a newly produced oligomerization catalyst or a regenerated oligomerization catalyst.
8. Process for the oligomerization according to embodiment 7, wherein the regenerated oligomerization catalyst is produced by step A), burning off of an oligomerization catalyst used for the oligomerization, and B) impregnating the oligomerization catalyst burnt off in step A) with a solution of a transition metal compound and subsequent calcination.
9. Process for the oligomerization according to embodiment 8, wherein in step B) the impregnated oligomerization catalyst is dried at temperatures between 100 and 250° C. and at standard pressure or under reduced pressure prior to the calcination.
10. Process for the oligomerization according to any of embodiments 1 to 9, wherein the oligomerization is carried out at a temperature in the range of 50 to 200° C. and at a pressure of 10 to 70 bar.

DETAILED DESCRIPTION OF THE INVENTION

The process according to the invention is a process for oligomerization of $C_3$- to $C_6$-olefins, in which a starting mixture is used comprising the $C_3$- to $C_6$-olefins and from which nitrogen-, oxygen- and/or sulfur-containing impurities that act as catalyst poisons have been at least partially removed,
wherein the oligomerization is carried out in at least two successive reaction stages, which each consist of at least one reactor and at least one distillation column, in each case using an oligomerization catalyst having a composition of 15 to 40% by weight NiO, 5 to 30% by weight $Al_2O_3$, 55 to 80% by weight $SiO_2$ and 0.01 to 2.5% by weight of an alkali metal oxide, and
wherein at least the reactor(s) of the first reaction stage are operated isothermally, characterized in that
the oligomerization catalyst in the first reaction stage is exchanged for a fresh oligomerization catalyst at the latest after 47 months, preferably at the latest after 45 months, particularly preferably at the latest after 43 months,
and the oligomerization catalyst in the following reaction stage(s) is exchanged for a fresh oligomerization catalyst at the earliest after 48 months to at the latest after 72 months.

In the context of the present invention, the term "reaction stage" encompasses from one or more reactors to one or more distillation columns. In the distillation columns, the remaining starting mixture comprising, for example, alkanes and unreacted olefins, are separated in particular from the product oligomers generated. Typical process-engineering ancillary units which can be incorporated in the reaction stages, such as preheaters for the feed, heat exchangers or similar, are not listed separately here but are familiar to those skilled in the art.

In the context of the present invention, the term "fresh oligomerization catalyst" means both newly produced catalysts and regenerated catalysts, which have already been used in a reactor for oligomerization, after removal but which have been regenerated by the method described below.

The process according to the invention, with respect to the statement of the number of months at which at the latest or from the earliest the catalyst is exchanged in a particular reaction stage, always refers to the last exchange of the catalyst in the particular reaction stage. In accordance with the invention, therefore, the first reaction stage has a shorter exchange interval than the subsequent reaction stage(s). Accordingly, the catalyst of the first reaction stage is changed at the latest 47 months after the use of this catalyst in the first reaction stage, and the catalysts in the subsequent reaction stage(s) therefore at the earliest 48 months after the use of these catalysts. The start time from which the number of months is counted can thus also be identical for the different stages, that is if the catalysts have last been changed at the same time.

With the procedure described for the exchange of the oligomerization catalysts, the time period of the catalyst exchange in which there is a decline in conversion can be significantly shortened. Surprisingly, it has been found that the catalyst in the reactor(s) of the first reaction stage ages more rapidly and/or is poisoned more rapidly than the catalysts in the subsequent reaction stage(s). If the catalyst in the reactor or reactors of the first reaction stage according to the invention is exchanged more frequently than in the subsequent reaction stage(s), the total time period of the exchange of catalyst of the following stage(s) is shortened since the catalyst now has to be exchanged less in a reaction stage.

It is true however that the added total time period in which an exchange of catalyst is carried out in all reaction stages is lengthened since, compared to the normal exchange, the catalyst in the reactor of the first reaction stage is exchanged more frequently. However, this goes along with the fact that the exchange of the remaining catalysts in the normal cycle of about 48 to 72 months can be conducted at the same time in all subsequent reaction stages and therefore the downtime is considerably lower overall. In addition, it is achieved by means of the procedure according to the invention that the catalyst activity in the reactor or reactors of the first reaction stage no longer decreases so sharply compared to a catalyst exchanged in the normal interval of 48 to 72 months since the time period which the catalyst is used and in which the ageing and poisoning processes can proceed is shorter.

As a result, it has been shown, surprisingly, that the conversion losses in the process according to the invention are lower overall and give higher conversions averaged over a long time period than in known processes in which the catalysts of all reaction stages are exchanged within the customary 48 to 72 months.

The process according to the invention is carried out broadly as follows: The starting point is a process for oligomerizing olefins in two or more, at least two, reaction stages. In the case of falling catalyst activity, which can be observed, for example, by GC analysis of the reaction products, the oligomerization catalyst is firstly exchanged in the first reaction stage, at the latest after 36 months from the start of use. For this purpose, the starting mixture comprising the olefins to be oligomerized is diverted around the first reaction stage and passed directly to the second reaction stage. The oligomerization catalyst can be removed from the reactor(s) of the first reaction stage that are now no longer charged with olefins. The reactor(s) of the bypassed reaction stage is then firstly purged with an inert gas in order to remove volatile organic substances. The reactor is then opened and the catalyst removed. As soon as the catalyst has been removed from the reactor(s), this is immediately filled with a fresh oligomerization catalyst. The reactor or reactors is/are then started up and the reaction stage, after completion of the start-up procedure, is again fully engaged as the first reaction stage. After 48 months up to at the latest 72 months, the catalyst is then exchanged in the second and possible further reaction stages present analogously to the procedure explained for the first reaction stage.

The process according to the invention comprises at least two reaction stages. In a preferred embodiment, the process for oligomerization comprises at maximum five reaction stages. Particularly preferred is a process regime with three, four or five reaction stages. Each of these reaction stages, independently of one another, comprises one or more reactors and one or more distillation columns in order to separate the oligomers formed from the residual starting mixture. It is also conceivable, however, that one of the reaction stages comprises two or more reactors, whereas in a preceding or subsequent reaction stage only one reactor is present.

The reactor(s) at least of the first reaction stage are operated isothermally, are thus cooled in a manner known to those skilled in the art, for example using a cooling medium, in order to maintain as far as possible a constant temperature across the reactor(s). In a preferred embodiment, all reactors in each reaction stage are operated isothermally. The reactor or reactors in one of the reaction stages, particularly the last reaction stage, can also be operated adiabatically. The expression "adiabatically operated" is to be understood to mean that the reactor(s) in the corresponding reaction stage are not actively cooled. Instead, the heat released during the oligomerization is carried from the reactor with the product stream, wherein less energy is required for evaporation in the downstream distillation column and the distillation can thus be carried out with a greater saving of energy.

In a further preferred embodiment, the volume of the reactor(s) of the second and each further reaction stage is equal to the volume of the preceding reaction stage or is in each case smaller than that of the preceding reaction stage since the amount of feed olefins in the respective streams of the second and each further reaction stage is typically lower.

Olefins employable for the process according to the invention are $C_3$- to $C_6$-olefins, preferably $C_3$- to $C_5$-olefins, particularly preferably $C_4$-olefins, or olefin mixtures based thereon which may also comprise proportions of analogous alkanes. Suitable olefins are, inter alia, α-olefins, n-olefins and cycloalkenes, preferably n-olefins. In a preferred embodiment, the olefin is n-butene.

The olefins are typically not used as reactants in pure form, but in available technical-grade mixtures. The term starting mixture used additionally in this invention is therefore to be understood as encompassing any type of mixtures containing the relevant olefins to be oligomerized in an amount which makes it possible to perform the oligomerization economically. The starting mixtures used in accordance with the invention preferably contain practically no further unsaturated compounds and polyunsaturated compounds such as dienes or acetylene derivatives. It is preferable to employ starting mixtures containing less than 5% by weight, in particular less than 2% by weight, of branched olefins based on the olefin proportion.

Propylene is produced on a large industrial scale by cracking of naphtha and is a commodity chemical which is readily available. $C_4$-olefins are present in light petroleum fractions from refineries or crackers. Technical mixtures which comprise linear $C_4$ olefins are light petroleum fractions from refineries, $C_4$ fractions from FC crackers or steam crackers, mixtures from Fischer-Tropsch syntheses, mixtures from the dehydrogenation of butanes, and mixtures formed by metathesis or from other industrial processes. Mixtures of linear butenes suitable for the process according to the invention are obtainable for example from the $C_4$-fraction of a steam cracker.

Butadiene is removed in the first step here. This is accomplished either by extraction (distillation) of the butadiene or by selective hydrogenation thereof. In both cases a virtually butadiene-free $C_4$-cut is obtained, the so-called raffinate II. In the second step, isobutene is removed from the $C_4$-stream, for example by production of MTBE by reaction with methanol. The now isobutene-free and butadiene-free $C_4$-cut, the so-called raffinate II, contains the linear butenes and any butanes. If at least some of the 1-butene obtained is removed therefrom, the so-called raffinate III is obtained.

In a preferred embodiment in the process according to the invention, $C_4$-olefin-containing streams are fed as starting mixture. Suitable olefin mixtures are particularly raffinate I and raffinate II and raffinate III.

It is known that the starting mixtures used in the process according to the invention which originate, for example, from steam crackers or catalytic crackers, may typically comprise nitrogen-, oxygen- and/or sulfur-containing impurities in the ppm range which act as catalyst poisons for the catalysts used. These impurities must therefore be removed from the starting mixture comprising the olefins to be oligomerized prior to the oligomerization. The starting mixture used in the process according to the invention is accordingly a starting mixture from which nitrogen-, oxygen- and/or sulfur-containing impurities that act as catalyst poisons have been at least partially removed.

The removal of nitrogen-, oxygen- and/or sulfur-containing impurities from hydrocarbon streams is known to those skilled in the art. For this purpose, the hydrocarbon streams used as starting mixture can be passed over, for example, one or more guard beds in which a material is present that takes up or adsorbs the impurities. A distillative removal of low-boiling or high-boiling impurities is also possible in some cases in upstream low boiler or high boiler columns. The impurities should therefore be removed from the hydrocarbon streams sufficiently so that poisoning of the catalyst in the oligomerization is retarded or completely prevented.

The reactor or reactors of the individual reaction stages each comprise an oligomerization catalyst having a composition of 15% to 40% by weight, preferably 15% to 30% by weight NiO, 5% to 30% by weight $Al_2O_3$, 55% to 80% by weight $SiO_2$ and 0.01% to 2.5% by weight, preferably 0.05% to 2% by weight, of an alkali metal oxide, preferably sodium oxide. The figures are based on a total composition of 100% by weight. In a particularly preferred embodiment of the present invention, the oligomerization catalyst is substantially free from titanium dioxide and/or zirconium dioxide, the oligomerization catalyst in particular comprising less than 0.5% by weight, preferably less than 0.1% by weight, particularly preferably less than 0.01% by weight, of titanium dioxide and/or zirconium dioxide in its total composition. The oligomerization catalyst in this case is particularly in the form of granules, an extrudate or in tablet form.

The (heterogeneous) oligomerization catalysts in the individual reactors of the reaction stages may in each case be independently selected oligomerization catalysts having the composition specified above.

The oligomerization catalyst according to the invention in principle comprises nickel oxide on an aluminosilicate support material. The support material can be an amorphous, mesoporous aluminosilicate, a crystalline, microporous aluminosilicate or an aluminosilicate having amorphous and crystalline phases. In the context of the present invention "amorphous" is to be understood as meaning the property of a solid which results from the fact that the solid has no crystal structure, i.e. no long-range order. However, it cannot be ruled out in the context of the present invention that the amorphous silica-alumina support material has small crystalline domains.

The oligomerization catalyst preferably has a specific surface area (calculated according to BET) of 150 to 700 m$^2$/g, more preferably 190 to 600 m$^2$/g, particularly preferably 220 to 550 m$^2$/g. The BET surface area is measured by nitrogen physisorption according to DIN ISO 9277 (2014-01 version).

The oligomerization catalysts present in the individual reactors in the reaction stages may be selected in each case independently of one another from the aforementioned substances. The individual oligomerization catalysts in the reactors are not always exactly identical here, but differ from each other in the composition, possibly only to a limited extent. This is also due to the fact that even if at the time point of the first start-up of the process according to the invention each reactor contains a fully identical catalyst composition, this composition changes with time during operation by the widest variety of effects over the course of the years (regenerated catalyst behaves differently to freshly produced catalysts, abrasion during operation, different ageing rates and/or poisoning, etc.). A reduction in conversion and/or selectivity (generally catalyst activity) during oligomerization due to ageing and/or poisoning may be encountered with increasing employment time of the oligomerization catalyst. The catalyst according to the invention is exchanged as described according to the invention and is replaced by a fresh oligomerization catalyst, i.e. a new or a regenerated oligomerization catalyst.

An oligomerization catalyst can be produced by the known processes of impregnation, wherein the support material is charged with a solution of a transition metal compound, especially a nickel compound, and is then calcined, or coprecipitation in which the entire catalyst composition is precipitated from a single, mostly aqueous solution. The oligomerization catalyst can also be produced by other processes familiar to those skilled in the art.

After use of the produced oligomerization catalyst in the oligomerization, the catalyst can also be regenerated in order to increase again the catalyst activity (for the oligomerization). The regeneration of the oligomerization catalyst in particular comprises the step A) of burning off and B) of the impregnation with a solution of a transition metal compound. In this case, the transition metal in the catalyst to be regenerated and the transition metal in the impregnation solution should be identical.

After use in oligomerization, the oligomerization catalyst may exhibit deposits of organic substances that require removal. Removal of the organic compounds deposited in the catalyst is preferably accomplished in step A) by simple burning off to form carbon oxides and water. The burn off in step A) may be carried out continuously or discontinuously in a furnace, for example in a rotary kiln or a shaft furnace. For this purpose the oligomerization catalyst (for example in the form of a granulate) is supplied to the furnace and preferably burnt off at a furnace temperature of 400° C. to 600° C., particularly preferably of 500° C. to 600° C. The burn off can be carried out using additionally supplied combustion air. This combustion air can be supplied in counter current and in addition further air is optionally blown into the oligomerization catalyst via suitable inlets to ensure rapid burn off.

Step B) comprises treating/impregnating the oligomerization catalyst burnt off in step A) with a solution of a transition metal compound, in particular a solution of a nickel compound, as step B1), and calcination of the treated oligomerization catalyst as step B2).

The performance of step B1) of the regeneration, in this example by nickel, is discussed below. However, the statements are also applicable to other transition metals.

The impregnation with nickel in step B1) may be effected similarly to the production of the oligomerization catalyst but optionally with the difference that a nickel solution having a lower nickel concentration than in the production of the oligomerization catalyst may be used. In principle any soluble nickel compound such as nickel nitrate ($Ni(NO_3)_2$), nickel acetate ($Ni(ac)_2$), nickel acetylacetonate ($Ni(acac)_2$), nickel sulfate ($NiSO_4$) or nickel carbonate ($NiCO_3$) may be used therefor to produce an aqueous or ammoniacal nickel solution.

The use of NiHAC solutions obtainable by dissolving nickel carbonate ($NiCO_3$) in concentrated ammonia solutions, optionally with addition of ammonium carbonate, has proven particularly advantageous. Such solutions may be used for the impregnation with nickel contents of 0.5 to 14% by weight, in particular of 2 to 10% by weight, especially preferably of 4 to 8% by weight.

For nickel application the oligomerization catalyst burned off in step A) is, for example, impregnated with a NiHAC solution having nickel contents of 0.5 to 14% by weight, in particular of 2% to 10% by weight, very particularly of 4% to 8% by weight until saturation of the pores present in the oligomerization catalyst. The impregnation may be performed with a process familiar to those skilled in the art such as for example by spraying until permanent appearance of a liquid film on the surface (incipient wetness). If the solution takeup is about 0.8 to 1.2 g of solution per g of oligomerization catalyst a deposition of about 0.5% to 6% by weight of additional nickel in the form of a basic carbonate can be achieved.

After step B1), the impregnated oligomerization catalyst can be dried in a suitable drying apparatus, for example a belt dryer with an air stream or else a conical dryer, at temperatures between 100° C. and 250° C., preferably between 120° C. and 220° C., and at standard pressure or else under vacuum, before calcination is conducted in step B2). By means of drying, water or excess ammonia in particular is discharged from the NiHAC solution.

The calcination of the oligomerization catalyst in step B2) may be carried out continuously or discontinuously in a suitable furnace, for example a shaft furnace or rotary kiln. In the case of continuous calcination, it is furthermore preferable when a gas is passed in counter current through the oligomerization catalyst, particularly in the form of a granulate. The gas employed may be air, nitrogen or a mixture thereof. The gas stream may be 0.2 to 4 m$^3$ of gas per kg of granulate per hour and the inlet temperature of the gas may be from 400° C. to 800° C., preferably 450° C. to 700° C. In addition to this heat introduced via the gas, energy may be introduced by active heating of the walls of the furnace.

The calcination temperature in the furnace in step B2) may be 400° C. to 800° C., preferably 450° C. to 700° C., particularly preferably 500° C. to 600° C. This temperature may be maintained over several 10 hours, preferably 5 to 60 hours, particularly preferably 10 to 40 hours, before the catalyst is cooled. Cooling is preferably carried out in a nitrogen stream. Air may additionally be added to the nitrogen and the amount of air should preferably be controlled. The amount of air preferably added to the nitrogen may be 100 to 10000 ppm by volume, preferably 300 to 7000 ppm by volume.

The oligomerization of the process according to the invention can be carried out at a temperature in the range from 50° C. to 200° C. by preference 60° C. to 180° C., preferably in the range from 60° C. to 130° C., and at a pressure of 10 to 70 bar, preferably of 20 to 55 bar. In a preferred embodiment of the present invention, the oligomerization is carried out in the liquid phase. If the oligomerization is to be carried out in the liquid phase the parameters pressure and temperature must to this end be chosen such that the reactant stream (the employed olefins or olefin mixtures) is in the liquid phase.

The weight-based space velocities (reactant mass per unit catalyst mass per unit time: weight hourly space velocity (WHSV)) are in the range between 1 g of reactant per g of catalyst and per h (=1 $h^{-1}$) and 190 $h^{-1}$, preferably between 2 $h^{-1}$ and 35 $h^{-1}$, particularly preferably between 3 $h^{-1}$ and 25 $h^{-1}$.

In one embodiment, particularly when using a catalyst comprising a nickel compound, preferably nickel oxide, on an aluminosilicate support, the degree of dimerization (also referred to as "percentage selectivity based on dimerization") after the oligomerization, based on the converted reactant, is at least 60%, more preferably at least 75%, particularly preferably at least 80%.

The linearity of an oligomerization product or of the dimers formed is described by the ISO index and represents a value for the average number of methyl branches in the dimer. For example (for butene as the reactant), n-octenes contribute 0, methylheptenes contribute 1 and dimethylhexenes contribute 2 to the ISO index of a $C_8$ fraction. The lower the ISO index, the more linear the construction of the molecules in the respective fraction. The ISO index is calculated according to the following general formula, wherein the proportion of the individual dimer fractions refers to the total dimer fraction:

$$\frac{\left(\begin{array}{l}\text{single-tracked dimers (wt \%) +}\\ 2\times \text{double-branched dimers (wt \%)}\end{array}\right)}{100}$$

Accordingly, a dimer mixture having an ISO index of 1.0 has an average of exactly 1 methyl branch per dimeric molecule.

The ISO index of the product from the oligomerization process according to the invention is preferably 0.8 to 1.2, more preferably 0.8 to 1.15.

The oligomers produced by the process according to the invention are utilized inter alia for producing aldehydes, alcohols and carboxylic acids. Thus for example the dimerizate of linear butenes affords a nonanal mixture by hydroformylation. This provides either the corresponding carboxylic acids by oxidation or a $C_9$-alcohol mixture by hydrogenation. The $C_9$ acid mixture may be used for producing lubricants or siccatives. The $C_9$-alcohol mixture is a precursor for the production of plasticizers, particularly dinonyl phthalates, or DINCH.

Even without further elaboration it is assumed that a person skilled in the art will be able to utilize the description above to the greatest possible extent. The preferred embodiments and examples are therefore to be interpreted merely as a descriptive disclosure which is by no means limiting in any way whatsoever.

The present invention is more particularly elucidated hereinbelow with reference to examples. Alternative embodiments of the present invention are obtainable analogously.

EXAMPLES

Example 1 (Non-Inventive)

In a 3-stage oligomerization plant, the catalyst charges of each stage are successively changed typically every 5 years. Such an exchange procedure takes approximately 21 days per stage. Under consideration here is a period of 15 years, where accordingly 3 stoppages take place to change the catalyst.

The 1st stage produces on average 570 tons of oligomerizate per day in the first 3 years using fresh catalyst. After a certain service life of the catalyst in the oligomerization reactor, the amount of oligomerizate produced decreases. After 3 years, i.e. in the 4th and 5th year, the first stage can then only produce 500 tons of oligomerizate per day.

The loss of activity in the 2nd and 3rd reaction stage is significantly lower and is neglected here. The 2nd stage produces on average 285 tons of oligomerizate per day during the 5 years. The 3rd stage produces on average 95 tons of oligomerizate per day during the 5 years.

Due to the 3 stoppages over the 15 years and the reduced activity of the 1st stage in each of the 2 years prior to exchange of the catalyst, approximately 208.7 kilotons of oligomerizate are lost overall.

Example 2 (Inventive)

In a 3-stage oligomerization plant, the catalyst charges are changed every 3 years in the 1st stage and every 5 years in the 2nd and 3rd stage. Such an exchange procedure takes 21 days per stage. Under consideration here is a period of 15 years, where accordingly 5 stoppages of the 1st reaction stage and 3 stoppages of the 2nd and 3rd reaction stage take place to change the catalyst.

The 1st stage produces on average 570 tons of oligomerizate per day in 3 years. The catalyst is changed prior to a significant decline in activity. The 2nd stage produces on average 285 tons of oligomerizate per day during the 5 years. The 3rd stage produces on average 95 tons of oligomerizate per day during the 5 years.

Due to the 5 stoppages of the 1st reaction stage and the 3 stoppages in the latter two stages over 15 years, 83.8 kilotons of oligomerizate are lost overall.

The amount of oligomerizate lost is therefore distinctly lower in the exchange cycle according to the invention. The more frequent changes of catalyst of the 1st reaction stage therefore enables the loss of activity and the accompanying shortfall in amount of oligomerizate to be more than compensated for in comparison to the non-inventive exchange cycle.

The invention claimed is:

1. A process for oligomerization of $C_3$- to $C_6$-olefins, the process comprising:
reacting a starting mixture comprising $C_3$- to $C_6$-olefins, from which nitrogen-, oxygen- and/or sulfur-containing impurities that act as catalyst poisons have been at least partially removed, in at least two successive reaction stages, wherein each reaction stage comprises at least one reactor and at least one distillation column, wherein each reaction stage uses an oligomerization catalyst, having a composition of 15 to 40% by weight NiO,
5 to 30% by weight $Al_2O_3$,
55 to 80% by weight $SiO_2$, and
0.01 to 2.5% by weight of an alkali metal oxide,
wherein the at least one reactor of the first reaction stage is operated isothermally,
exchanging the oligomerization catalyst in the first reaction stage for a fresh oligomerization catalyst at the latest after 47 months, and
exchanging the oligomerization catalyst in the second reaction stage for a fresh oligomerization catalyst at the earliest after 48 months to at the latest after 72 months.

2. The process according to claim 1, wherein the exchanging the oligomerization catalyst in the first reaction stage for the fresh oligomerization catalyst occurs at the earliest after 6 months.

3. The process according to claim 1, wherein the process comprises three, four or five reaction stages.

4. The process according to claim 3, wherein the oligomerization catalyst of the second and all subsequent reaction stages are exchanged at the same time.

5. The process according to claim 1, wherein the at least one reactor in each reaction stage is operated isothermally.

6. The process according to claim 1, wherein the volume of the reactor of the second reaction stage and, if present, the volume of the reactor of each subsequent reaction stage is equal to or smaller than the volume of the preceding reaction stage.

7. The process according to claim 1, wherein the fresh oligomerization catalyst is a newly produced oligomerization catalyst or a regenerated oligomerization catalyst.

8. The process according to claim 7, wherein the fresh oligomerization catalyst is a regenerated oligomerization catalyst produced by:
A) burning off an oligomerization catalyst used for the oligomerization, and
B) impregnating the oligomerization catalyst burnt off in A) with a solution of a transition metal compound and subsequent calcination.

9. The process according to claim 8, wherein in B), the impregnated oligomerization catalyst is dried at temperatures between 100 and 250° C. and at standard pressure or under reduced pressure prior to the calcination.

10. The process according to claim 1, wherein the oligomerization is carried out at a temperature in the range of 50 to 200° C. and at a pressure of 10 to 70 bar.

11. The process according to claim 1, wherein the oligomerization catalyst in the first reaction stage is exchanged at the latest after 45 months.

12. The process according to claim 1, wherein the oligomerization catalyst in the first reaction stage is exchanged at the latest after 43 months.

13. The process according to claim 1, wherein the $C_3$- to $C_6$-olefins are purified by completely removing the nitrogen-, oxygen- and/or sulfur-containing impurities from the starting mixture comprising the $C_3$- to $C_6$-olefins.

14. A system for oligomerization of $C_3$- to $C_6$-olefins, the system comprising:
a starting mixture comprising the $C_3$- to $C_6$-olefins, wherein nitrogen-, oxygen- and/or sulfur-containing impurities that act as catalyst poisons are at least partially removed from the starting mixture,
at least two reaction stages, each of which comprises at least one reactor and at least one distillation column, and
an oligomerization catalyst, comprising
15 to 40% by weight NiO,
5 to 30% by weight $Al_2O_3$,
55 to 80% by weight $SiO_2$, and
0.01 to 2.5% by weight of an alkali metal oxide,
wherein the at least one reactor of the first reaction stage is operated isothermally, wherein the oligomerization catalyst in the first reaction stage is exchanged with a fresh oligomerization catalyst at the latest after 47 months, and wherein the oligomerization catalyst in the second reaction stage is exchanged with a fresh oligomerization catalyst at the earliest after 48 months to at the latest after 72 months.

* * * * *